(12) United States Patent
Hu et al.

(10) Patent No.: US 12,153,033 B2
(45) Date of Patent: Nov. 26, 2024

(54) COMBUSTIBLE GAS SENSOR MODULE AND COMBUSTIBLE GAS SENSING DEVICE

(71) Applicant: Gulf Security Technology Co., Ltd., Qinhuangdao (CN)

(72) Inventors: Jinli Hu, Qinhuangdao (CN); Maoqing Yang, Qinhuangdao (CN)

(73) Assignee: GULF SECURITY TECHNOLOGY CO., LTD., Qinhuangdao (CN)

( * ) Notice: Subject to any disclaimer, the term of this patent is extended or adjusted under 35 U.S.C. 154(b) by 290 days.

(21) Appl. No.: 17/730,699

(22) Filed: Apr. 27, 2022

(65) Prior Publication Data

US 2022/0341905 A1  Oct. 27, 2022

(30) Foreign Application Priority Data

Apr. 27, 2021 (CN) .......................... 202110459264.3

(51) Int. Cl.
*G01N 33/00* (2006.01)

(52) U.S. Cl.
CPC ..... *G01N 33/0057* (2013.01); *G01N 33/0006* (2013.01)

(58) Field of Classification Search
CPC ........... G01N 33/0006; G01N 33/0008; G01N 33/0027; G01N 33/0057; G01N 2035/00326; G01N 2201/024
See application file for complete search history.

(56) References Cited

U.S. PATENT DOCUMENTS

| 4,352,099 A | 9/1982 | Christen et al. |
| 5,582,797 A | 12/1996 | Kewley et al. |
| 6,202,472 B1 | 3/2001 | Wezurek et al. |
| 6,799,984 B2 * | 10/2004 | Starta ..................... H01R 13/71 439/246 |
| 7,089,778 B2 | 8/2006 | Rabenecker et al. |
| 7,310,991 B2 | 12/2007 | Lange et al. |

(Continued)

FOREIGN PATENT DOCUMENTS

| CN | 204374162 U | 6/2015 |
| CN | 107561208 A | 1/2018 |

(Continued)

OTHER PUBLICATIONS

Unknown Author; "Honeywell Analytics Sensepoint XCD Explosion-Proof Transmitter for Hazardous Gas Detection"; Lesman Instrument Company; 1995-2021; 2 Pages. https://www.lesman.com/honeywell-analytics-sensepoint-xcd-explosion-proof-transmitter-for-hazardous-gas-detection.

(Continued)

*Primary Examiner* — Justin N Olamit (74) *Attorney, Agent, or Firm* — CANTOR COLBURN LLP (57) ABSTRACT

A combustible gas sensor module and a combustible gas sensing device. The combustible gas sensor module includes an enclosure including a first end and a second end opposite to each other; a plug connector disposed at the first end of the enclosure for connecting to a sensing device body of a combustible gas sensing device; a sensor unit disposed at the second end of the enclosure for sensing combustible gas; and a circuit board disposed in the enclosure and respectively connected to the plug connector and the sensor unit, with a microcontroller provided thereon.

7 Claims, 6 Drawing Sheets

(56) References Cited

U.S. PATENT DOCUMENTS

| | | | |
|---|---|---|---|
| 8,934,263 B2* | 1/2015 | Eckhardt | G01L 19/0654 |
| | | | 73/756 |
| 9,075,029 B2* | 7/2015 | Adami | G01N 33/0006 |
| 9,739,759 B2* | 8/2017 | Matsui | B01D 46/0002 |
| 9,778,217 B2 | 10/2017 | Liu et al. | |
| 10,024,698 B2 | 7/2018 | Landis | |
| 10,316,984 B2* | 6/2019 | Landis | G01L 19/147 |
| 10,617,985 B2 | 4/2020 | Morris et al. | |
| 10,976,292 B2* | 4/2021 | Lindsey | G01F 23/18 |
| 2016/0109419 A1 | 4/2016 | Matsui et al. | |
| 2018/0058887 A1 | 3/2018 | Gindele et al. | |
| 2020/0103386 A1 | 4/2020 | Lindsey et al. | |

FOREIGN PATENT DOCUMENTS

| | | | |
|---|---|---|---|
| CN | 207051187 U | | 2/2018 |
| CN | 207114410 U | | 3/2018 |
| CN | 210269686 U | | 4/2020 |
| CN | 111721817 A | * | 9/2020 |
| CN | 111766340 A | | 10/2020 |
| GB | 2467413 B | | 12/2010 |
| JP | 4578990 B2 | | 11/2010 |
| JP | 4652964 B2 | | 3/2011 |
| KR | 200321771 Y1 | | 7/2003 |
| KR | 101400777 B1 | | 5/2014 |
| RU | 2675776 C1 | | 12/2018 |

OTHER PUBLICATIONS

European Search Report for Application No. 22169970.5; Issued Sep. 16, 2022; 8 Pages.

* cited by examiner

COMBUSTIBLE GAS SENSOR MODULE AND COMBUSTIBLE GAS SENSING DEVICE

FOREIGN PRIORITY

This application claims priority to Chinese Patent Application No. 202110459264.3, filed Apr. 27, 2021, and all the benefits accruing therefrom under 35 U.S.C. § 119, the contents of which in its entirety are herein incorporated by reference.

TECHNICAL FIELD OF INVENTION

The present invention relates to the field of combustible gas sensing, in particular to a combustible gas sensor module and a combustible gas sensing device.

BACKGROUND OF THE INVENTION

In industrial or commercial places, combustible gas detectors are often used to detect the leakage of combustible gas, and to issue an alarm when the combustible gas leaks. A combustible gas detector usually comprises an enclosure, a circuit board, a main controller, a display and other components as well as a gas sensor integrated in it, and the calibration, installation and testing thereof are completed by the manufacturer. Gas sensors often employ catalytic combustion type sensors with a service life of about three years. As the gas sensor is integrated in the combustible gas sensing device, the entire combustible gas sensing device needs to be replaced when the gas sensor fails.

SUMMARY OF THE INVENTION

The objective of the present invention is to solve or at least alleviate the problems existing in the prior art.

According to one aspect, a combustible gas sensor module is provided, which comprises: an enclosure comprising a first end and a second end that are opposite to each other; a plug connector disposed at the first end of the enclosure for connecting to a sensing device body of a combustible gas sensing device; a sensor unit disposed at the second end of the enclosure for sensing combustible gas; and a circuit board disposed in the enclosure and respectively connected to the plug connector and the sensor unit, with a microcontroller provided thereon.

Optionally, in the combustible gas sensor module, the circuit board comprises a first side and a second side that are opposite to each other, and the sensor unit is mounted on the first side of the circuit board and extends out of the second end of the enclosure from an opening at the second end of the enclosure.

Optionally, in the combustible gas sensor module, the second side of the circuit board is connected to the plug connector through connecting wires, and the microcontroller is disposed on the second side of the circuit board.

Optionally, in the combustible gas sensor module, a flexible buffer gasket is provided around the sensor unit outside the second end of the enclosure.

Optionally, in the combustible gas sensor module, the plug connector has a foolproof groove or protrusion.

Optionally, in the combustible gas sensor module, the enclosure is cylindrical, the end face of the first end of the enclosure has a cylindrical protrusion with internal threads, the plug connector has external threads and is fixed to the enclosure through cooperation of the external threads and the internal threads, and the end face of the second end of the enclosure has an opening from which the sensor unit extends out of the enclosure.

Optionally, in the combustible gas sensor module, the combustible gas sensor module can be used to sense a plurality of gases, and the microcontroller, based on the types of gases to be sensed, calibrates preset parameters of the combustible gas sensor module.

According to another aspect, a combustible gas sensing device is provided, which comprises: a sensing device body; and the combustible gas sensor module according to various embodiments that is detachably mounted to the sensing device body.

Optionally, in the combustible gas sensing device, the combustible gas sensor module is connected to the corresponding plug port of the sensing device body through a plug connector, and the combustible gas sensing device further comprises a cover cap connected to the sensing device body, such that the cover cap abuts against a flexible buffer gasket outside the second end of the enclosure of the combustible gas sensor module, thereby firmly positioning the combustible gas sensor module between the cover cap and the sensing device body.

Optionally, in the combustible gas sensing device, the inside of the cover cap comprises an explosion-proof metal mesh surrounding the exposed portion of the sensor unit, the explosion-proof metal mesh is fixed to the cover cap, and vent holes are respectively provided on the bottom wall and the side wall near the bottom of the cover cap.

The combustible gas sensor module according to the embodiments of the present invention can be easily replaced.

BRIEF DESCRIPTION OF THE DRAWINGS

With reference to the accompanying drawings, the disclosure of the present invention will become easier to understand. Those skilled in the art would easily understand that these drawings are for the purpose of illustration, and are not intended to limit the protection scope of the present invention. In addition, in the figures, similar numerals are used to denote similar components, wherein.

DETAILED DESCRIPTION OF THE INVENTION

Figure 1:
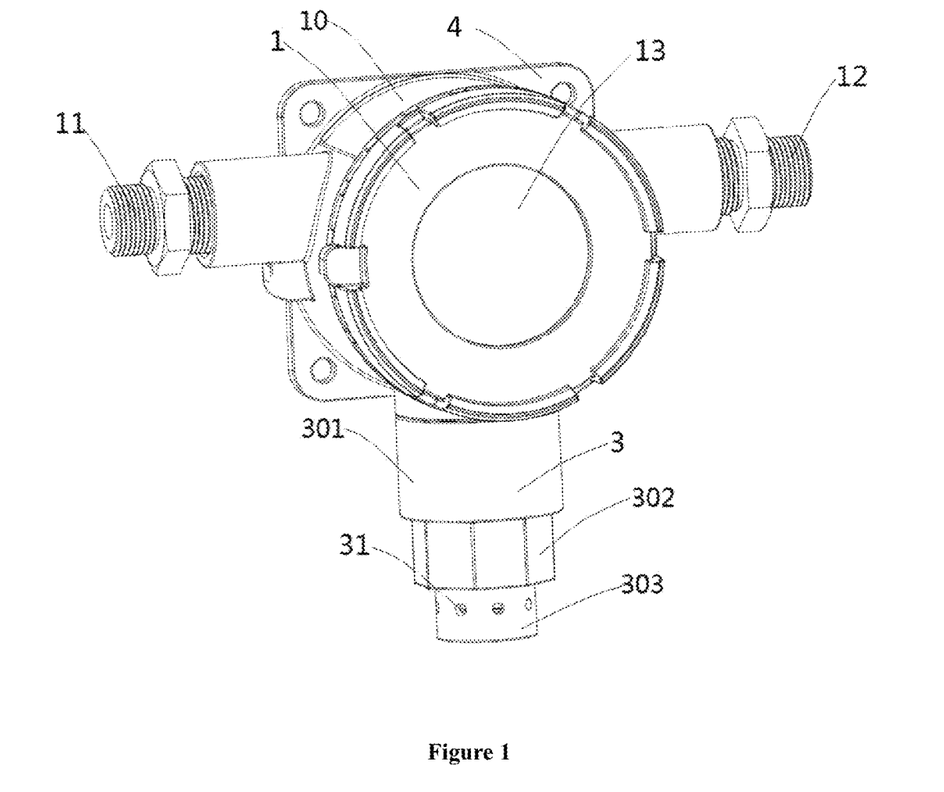
FIGS. 1 and 2 respectively illustrate perspective views from different angles of a combustible gas sensing device according to an embodiment.
Figure 2:
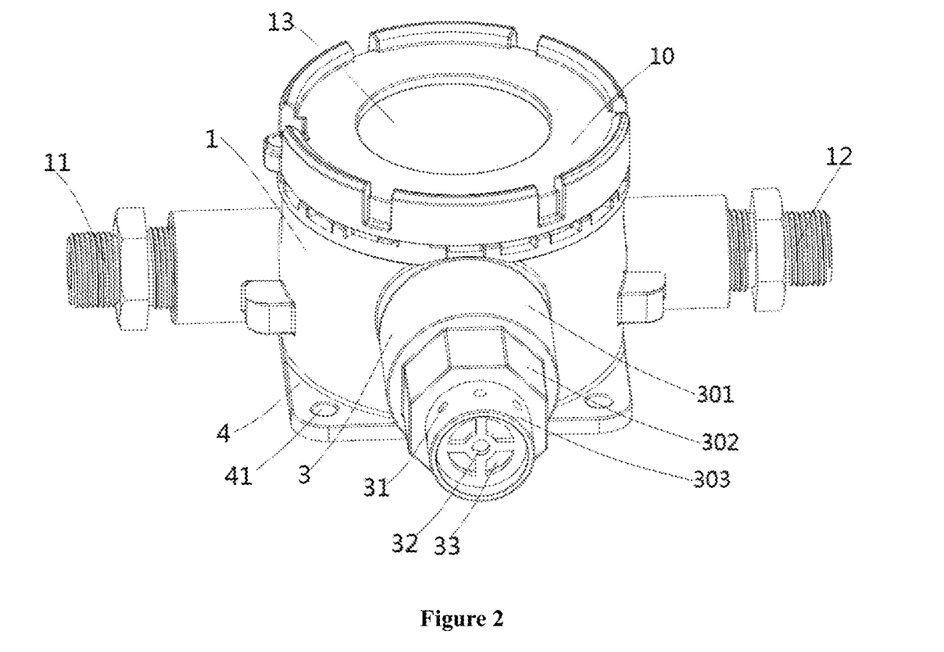

First, a combustible gas sensing device according to an embodiment of the present invention will be introduced with reference to FIGS. 1 and 2. The combustible gas sensing device according to the embodiment of the present invention may be arranged in an industrial or commercial place to detect combustible gas, such as natural gas, liquefied petroleum gas, etc., and to issue an alarm when a combustible gas leakage occurs. The combustible gas sensing device according to the embodiment may be arranged individually, or a plurality of (e.g., dozens or even hundreds of) combustible gas sensing devices according to the embodiment may be arranged in one area, and these combustible gas sensing devices are connected to the same control host. The combustible gas sensing device according to the embodiment comprises: a sensing device body 1; and a combustible gas sensor module 2 detachably mounted to the sensing device body 1. In FIGS. 1 and 2, the combustible gas sensor module 2 is disposed inside a cover cap 3, so it is hidden from view by the cover cap 3. Therefore, the combustible gas sensor module 2 will be described in more detail below with reference to FIGS. 3 to 6.

The sensing device body 1 of the combustible gas sensing device according to the embodiment may comprise a housing 10, which is, for example, substantially cylindrical as shown in the figures, and may be provided with, for example, a display device 13 on its front end face. In the figures, a first line port 11 and a second line port 12, which can be used respectively as an incoming line port and an outgoing line port, are provided respectively on the left and right sides of the housing 10, thereby achieving the connection of a plurality of combustible gas sensing devices according to the embodiment. For example, the first line port 11 of the following combustible gas sensing device is connected to the second line port 12 of the preceding combustible gas sensing device. A plurality of combustible gas sensing devices that are connected to each other may be connected, for example, to the same power supply and control host, and the first line port 11 and the second line port 12 may be used for power supply and/or transmission of data signals. The inside of the housing may be provided with electrical components such as circuit boards, processors, and memories, and the display device 13 may display information such as gas concentration, and may include warning lights and the like. In some embodiments, the sensing device body 1 may also be integrated with a buzzer and the like. The back side of the housing 10 opposite to the display device 13 may be provided with a flange 4, which may be, for example, a square shape, and the four corners thereof protruding from the housing 10 are provided with mounting holes 41 for fixed installation of the combustible gas sensing device. As shown in FIG. 1, a mounting port of the combustible gas sensor module 2 and a cover cap 3 are provided in the lower portion of the housing 10. The cover cap 3 is detachably mounted to the lower portion of the housing 10 so as to position the combustible gas sensor module 2 between the cover cap 3 and the housing 10. The cover cap 3 generally comprises an upper portion 301 for connecting to the sensing device body 1, a middle portion 302 having an outer octagonal contour, and a bottom portion 303 having vent holes. In some embodiments, the side wall of the bottom portion 303 of the cover cap 3 is provided with vent holes 31, and the bottom of the bottom portion 303 of the cover cap 3 is provided with a central vent hole 32 and peripheral fan-shaped vent holes 33. These vent holes 31, 32, 33 allow ambient gas to enter into the cover cap 3 to be sensed by a sensor unit 25 of the combustible gas sensor module 2 in order to detect, for example, whether a specific gas concentration in the ambient gas exceeds a reference value.

Referring now to FIGS. 3 to 6, the structure of the combustible gas sensor module 2 according to the embodiment and its assembly relationship with the sensing device body 1 will be described in more detail. It should be noted that the combustible gas sensor module 2 according to the embodiment of the present invention is detachable and replaceable. Therefore, when the combustible gas sensor module 2 fails to function properly due to service life or other reasons, only the combustible gas sensor module 2 is to be replaced, while the entire combustible gas sensing device needs not to be replaced. The combustible gas sensor module 2 comprises: an enclosure 20 having a first end 21 and a second end 22 that are opposite to each other; a plug connector 23 disposed at the first end 21 of the enclosure, such as protruding from the first end 21 of the enclosure, which is used to connect to the sensing device body of the combustible gas sensing device, for example, for transmitting signals and electricity; a sensor unit 25 disposed at the second end 22 of the enclosure, wherein the sensor unit 25 extends out of the enclosure 20 from inside of the enclosure 20, and have an exposed portion protruding beyond the second end 22 of the enclosure 20 for sensing combustible gas; and a circuit board 27 (see FIG. 6) respectively connected to the plug connector 23 and the sensor unit 25, with a microcontroller provided thereon. The combustible gas sensor module 2 according to the embodiment of the present invention, on the one hand, is replaceable, and on the other hand, has a circuit board and a microcontroller, and thus parameter calibration for special gases can be completed by the manufacturer before selling. As such, when using the combustible gas sensor module 2, the user only needs to complete a simple installation without re-calibration or debugging. In some embodiments, the combustible gas sensor module 2 can be used to sense a variety of different combustible gases, and the manufacturer can, based on the types of gases to be sensed through the microcontroller, calibrate the preset parameters of the combustible gas sensor module 2.

In some embodiments, the circuit board 27 comprises a first side and a second side that are opposite to each other. In the case of the orientation shown in FIG. 6, the first side is the lower side as shown and the second side is the upper side as shown, wherein, the sensor unit 25 is mounted directly on the first side of the circuit board 27 and extends out of the enclosure 20 from an opening 29 at the second end 22 of the enclosure. In some embodiments, the second side of the circuit board 27 is connected to a plug connector 23 through connecting wires 28. In addition, a microcontroller may be provided on the second side of the circuit board 27.

Figure 3:
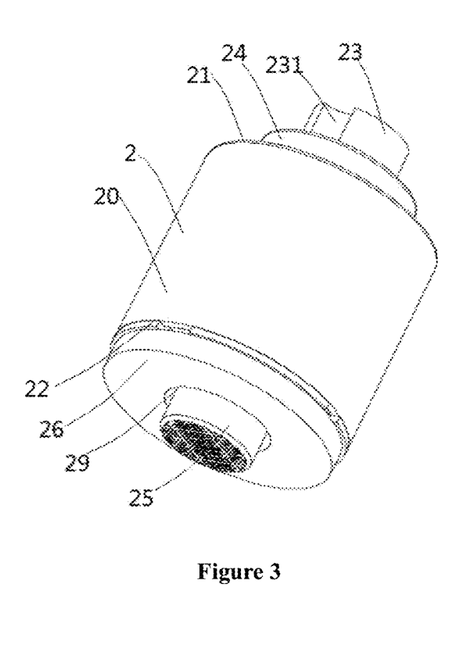
FIGS. 3 and 4 respectively illustrate perspective views from different angles of a combustible gas sensor module according to an embodiment.
Figure 4:
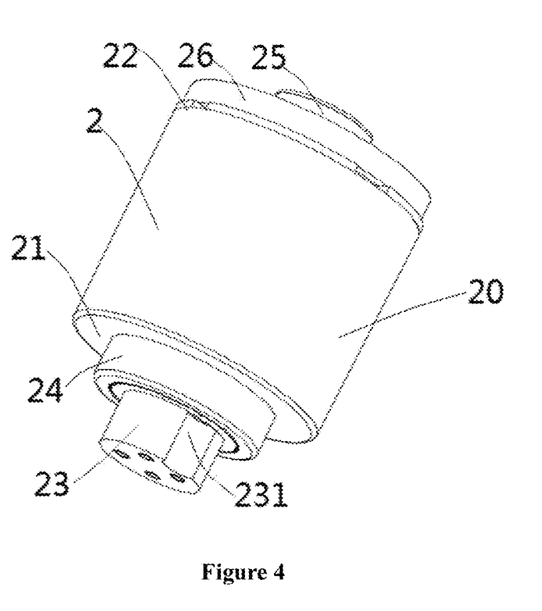
Figure 5:
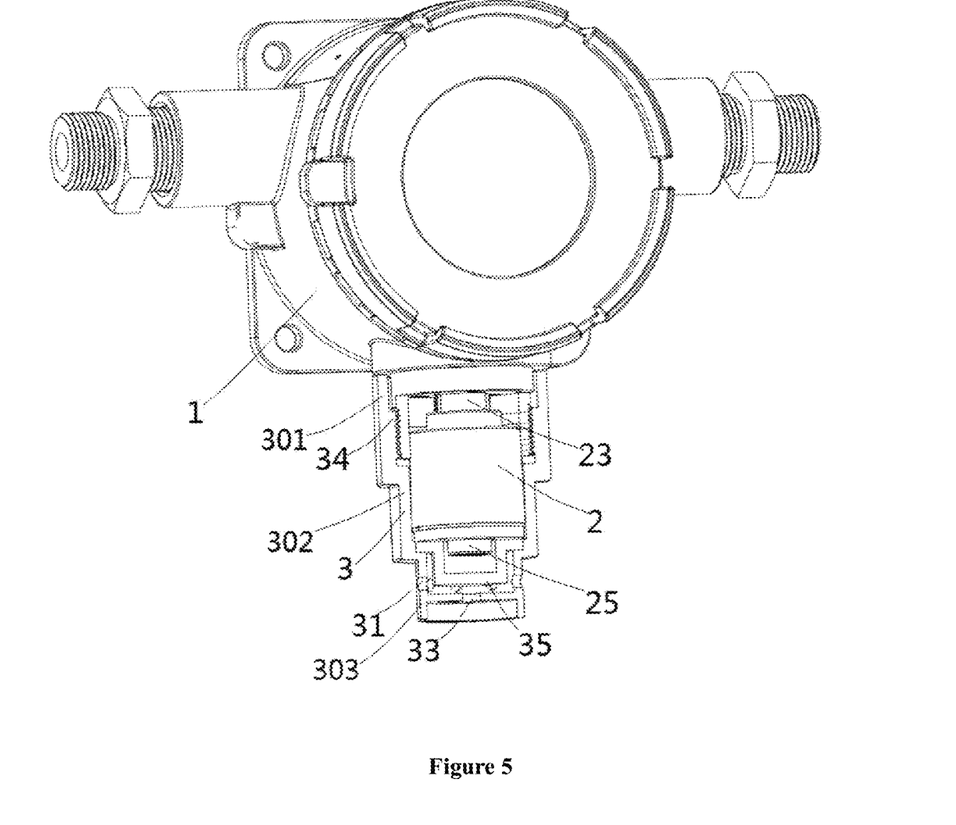
FIG. 5 illustrates a partial internal structure of a combustible gas sensing device according to an embodiment.
Figure 6:
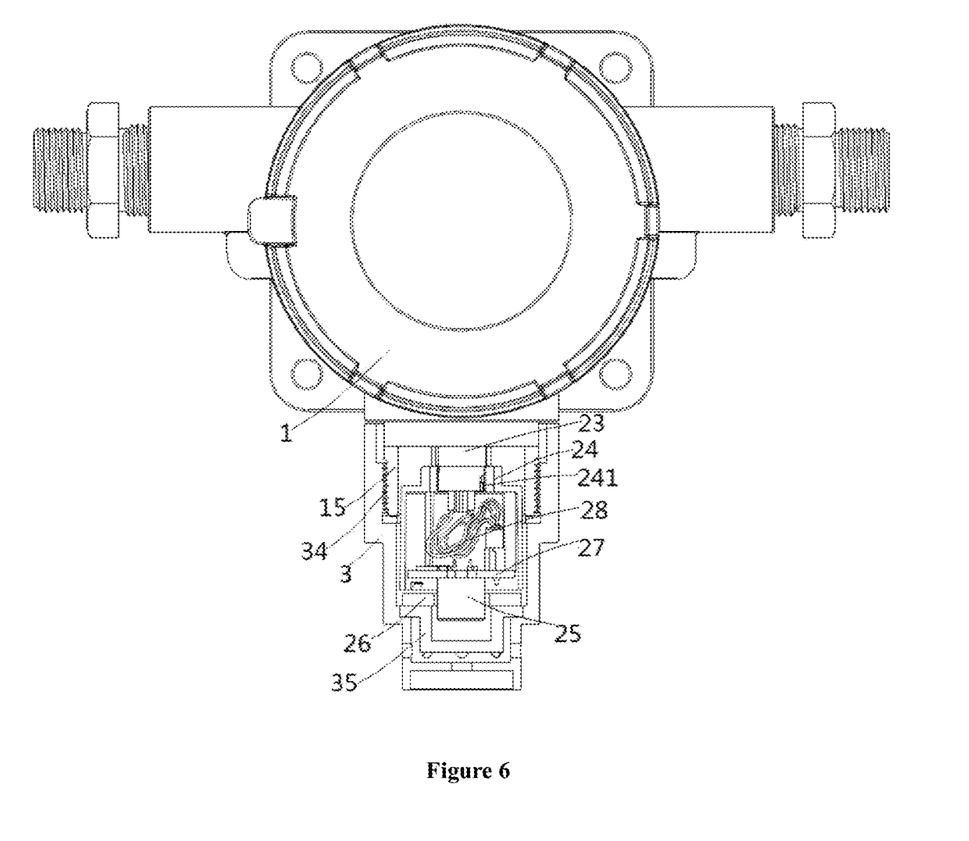
FIG. 6 illustrates a partial cross-sectional view of a combustible gas sensing device according to an embodiment.

As shown in FIG. 3, in some embodiments, a flexible buffer gasket 26, such as an elastic foam or a rubber pad, is provided around the sensor unit 25 outside the second end 22 of the enclosure. Alternatively, a flexible buffer gasket 26 may also be provided at the first end of the enclosure or in the cover cap 3. After the combustible gas sensor module 2 is mounted in place, the inside of the cover cap 3 abuts against and presses the flexible buffer gasket 26 to better limit the position of the combustible gas sensor module 2 to prevent it from vibrating. As shown in FIG. 4, in some embodiments, the plug connector 23 at the first end of the enclosure has a foolproof design, such as a groove 231 or a protrusion, to ensure accurate installation of the plug connector 23.

In some embodiments, the enclosure 20 of the combustible gas sensor module 2 is cylindrical, the end face of the first end 21 of the enclosure 20 has a cylindrical protrusion 24 with internal threads 241 (FIG. 6) for receiving the plug connector 23, and the plug connector 23 may have external threads so as to be screwed into the cylindrical protrusion 24, thereby being secured at the first end 21 of the enclosure 20. In addition, the end face of the second end 22 of the enclosure has an opening, and the sensor unit 25 can be mounted on the circuit board 27 and extends out of the enclosure from the opening of the second end of the enclosure, protruding beyond the second end of the enclosure and the optional flexible buffer gasket 26.

When replacing the combustible gas sensor module 2, the cover cap 3 should first be removed. For example, the cover cap 3 may, through the internal threads 34 on its upper portion 301, also be screwed into the external threads on the port at the bottom of the housing 10 of the sensing device body 1. As clearly shown in FIGS. 1 and 2, the middle portion 302 of the cover cap 3 may have an outer octagonal portion to facilitate its installation and removal. After removing the cover cap 3, it is only necessary to pull out the combustible gas sensor module 2 and replace it with a new one. Finally, the cover cap 3 is mounted again. At this time, as the cover cap 3 is being tightened, it squeezes the flexible buffer gasket 26 of the combustible gas sensor module 2, thereby stably positioning the combustible gas sensor module 2 between the housing 10 of the sensing device body 1 and the cover cap 3. In some embodiments, the inside of the cover cap 3 comprises an explosion-proof metal mesh 35 surrounding the exposed portion of the sensor unit. The explosion-proof metal mesh 35 may be cup-shaped, which can allow gas to pass through, and at the same time can protect the sensor unit 25 when an explosion occurs outside. The explosion-proof metal mesh 35 can be fixed to the cover cap 3, for example, by welding its edges to the inside of the cover cap 3. The combustible gas sensor module 2 according to the embodiment of the present invention can be easily replaced by the user, and it can be pre-calibrated by the manufacturer, which saves on-site calibration or debugging.

The specific embodiments described above are merely intended to describe the principles of the present invention more clearly, wherein various components are clearly shown or described to facilitate the understanding of the principles of the present invention. Those skilled in the art may, without departing from the scope of the present invention, make various modifications or changes to the present invention. Therefore, it should be understood that these modifications or changes should be included within the scope of patent protection of the present invention.

What is claimed is:

1. A combustible gas sensor module, comprising:
   an enclosure comprising a first end and a second end opposite to each other;
   a plug connector disposed at the first end of the enclosure for connecting to a sensing device body of a combustible gas sensing device;
   a sensor unit disposed at the second end of the enclosure for sensing combustible gas; and
   a circuit board disposed in the enclosure and respectively connected to the plug connector and the sensor unit, with a microcontroller provided on the circuit board;
   wherein the combustible gas sensor module is configured to sense a plurality of gases, and the microcontroller calibrates preset parameters of the combustible gas sensor module in response to a type of gas to be sensed such that the gas sensor module is pre-calibrated;
   wherein the circuit board comprises a first side and a second side opposite to each other, and the sensor unit is mounted on the first side of the circuit board and extends out of the second end of the enclosure from an opening at the second end of the enclosure.

2. The combustible gas sensor module according to claim 1, wherein the second side of the circuit board is connected to the plug connector through connecting wires, and the microcontroller is disposed on the second side of the circuit board.

3. The combustible gas sensor module according to claim 1, wherein a flexible buffer gasket is provided around the sensor unit outside the second end of the enclosure.

4. The combustible gas sensor module according to claim 1, wherein the plug connector has a foolproof groove or a protrusion.

5. A combustible gas sensor module, comprising:
   an enclosure comprising a first end and a second end opposite to each other;
   a plug connector disposed at the first end of the enclosure for connecting to a sensing device body of a combustible gas sensing device;
   a sensor unit disposed at the second end of the enclosure for sensing combustible gas; and
   a circuit board disposed in the enclosure and respectively connected to the plug connector and the sensor unit, with a microcontroller provided on the circuit board;
   wherein the combustible gas sensor module is configured to sense a plurality of gases, and the microcontroller calibrates preset parameters of the combustible gas sensor module in response to a type of gas to be sensed such that the gas sensor module is pre-calibrated;
   wherein the enclosure is cylindrical, an end face of the first end of the enclosure has a cylindrical protrusion with internal threads, the plug connector has external threads and is fixed to the enclosure through cooperation of the external threads and the internal threads, and an end face of the second end of the enclosure has an opening from which the sensor unit extends out of the enclosure.

6. A combustible gas sensing device, comprising:
   a sensing device body; and
   a combustible gas sensor module mounted to the sensing device body;
   the combustible gas sensor module, including:
   an enclosure comprising a first end and a second end opposite to each other;
   a plug connector disposed at the first end of the enclosure for connecting to a sensing device body of a combustible gas sensing device;
   a sensor unit disposed at the second end of the enclosure for sensing combustible gas; and
   a circuit board disposed in the enclosure and respectively connected to the plug connector and the sensor unit, with a microcontroller provided on the circuit board;
   wherein the combustible gas sensor module is configured to sense a plurality of gases, and the microcontroller calibrates preset parameters of the combustible gas sensor module in response to a type of gas to be sensed such that the gas sensor module is pre-calibrated;
   wherein the combustible gas sensor module is connected to a corresponding plug port of the sensing device body through the plug connector, and the combustible gas sensing device further comprises a cover cap connected to the sensing device body, such that the cover cap abuts against a flexible buffer gasket outside the second end of the enclosure of the combustible gas sensor module, thereby firmly positioning the combustible gas sensor module between the cover cap and the sensing device body.

7. The combustible gas sensing device according to claim 6, wherein an inside of the cover cap comprises an explosion-proof metal mesh surrounding an exposed portion of the sensor unit, the explosion-proof metal mesh is fixed to the cover cap, and vent holes are respectively provided on side wall and bottom wall of the bottom of the cover cap.

\* \* \* \* \*